United States Patent [19]

Schlein

[11] 4,239,045
[45] Dec. 16, 1980

[54] SURGICAL KNIFE

[76] Inventor: Allen P. Schlein, 107 Curtis Ter., Fairfield, Conn. 06430

[21] Appl. No.: 26,836

[22] Filed: Apr. 4, 1979

[51] Int. Cl.³ .............................................. A61B 17/32
[52] U.S. Cl. ..................................................... 128/305
[58] Field of Search ............... 128/305, 304, 751, 757; 30/287, 294, 299, 314

[56] References Cited

U.S. PATENT DOCUMENTS

| 1,790,014 | 1/1931 | Mikitta | 30/287 |
| 2,583,750 | 1/1952 | Runnels | 128/304 |
| 2,693,028 | 11/1954 | Stoddard | 30/121 |
| 3,221,744 | 12/1965 | Stryker | 128/305 |
| 3,477,435 | 11/1969 | Artelli | 128/304 |
| 3,835,859 | 9/1974 | Roberts et al. | 128/305 |

OTHER PUBLICATIONS

"A Flexible Meniscotomy Knife," *The Journal of Bone and Joint Surgery*, Jul. 1958.

Primary Examiner—Robert W. Michell
Assistant Examiner—Michael H. Thaler
Attorney, Agent, or Firm—Spencer E. Olson

[57] ABSTRACT

A knife particularly adapted for use in removing the semilunar cartilages from the knee has an elongated handle-engaging shank and two cutting blades fixed forwardly thereon. A first of the blades is flat transversely and concave longitudinally in extension of the shank with a curvature generally conforming to the curvature of the outer surface of the meniscus, and has a cutting edge at its front end. The second blade is integrally joined to the first blade along one edge thereof and is disposed at a right angle to the concave side of the first blade, and tapers rearwardly from its forward cutting edge toward the shank. A guide member projects forwardly from the point of intersection of the cutting edges of the two blades.

4 Claims, 3 Drawing Figures

U.S. Patent  Dec. 16, 1980  4,239,045
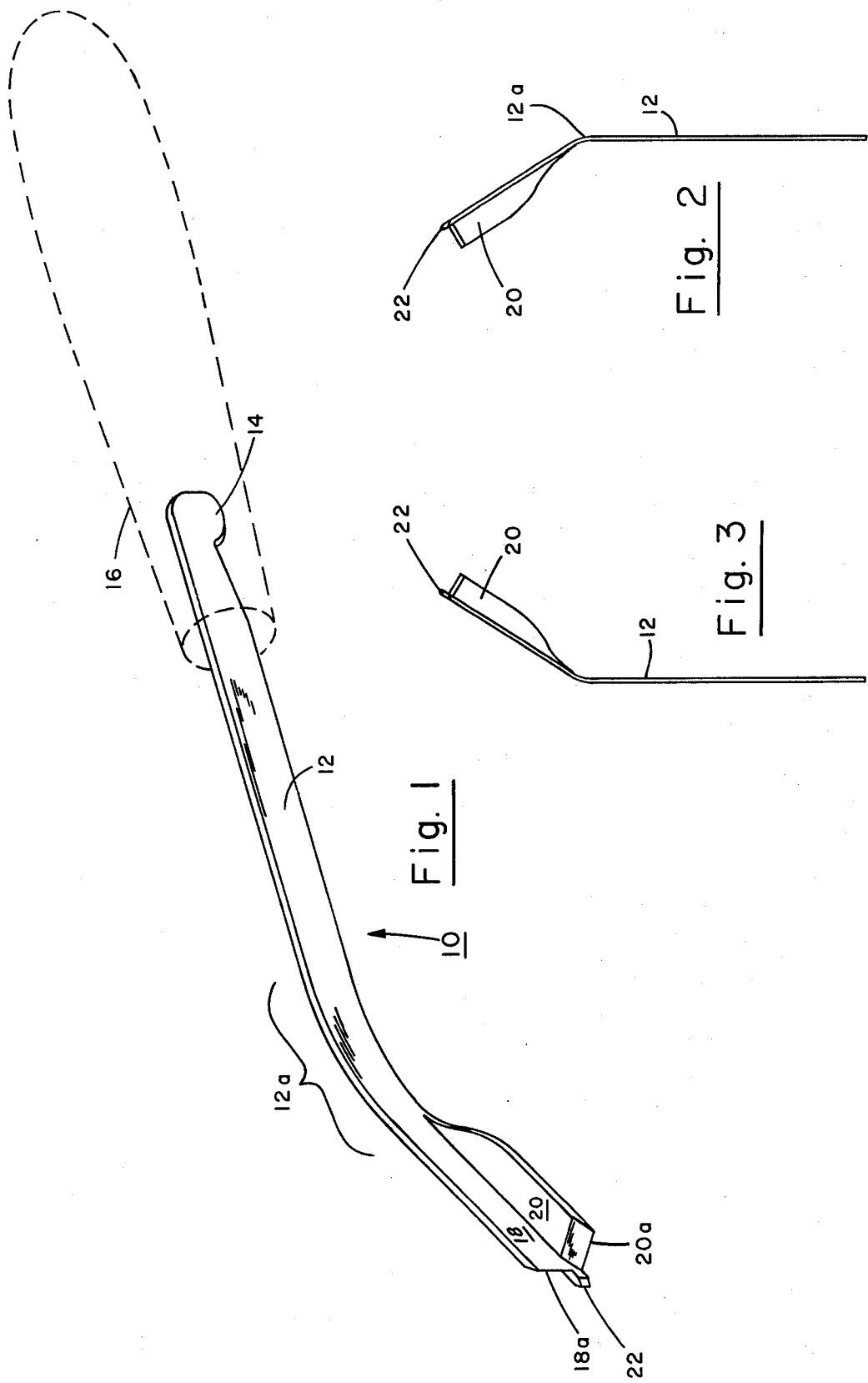

SURGICAL KNIFE

BACKGROUND OF THE INVENTION

This invention relates in general to cutting instruments and, more particularly, to a surgical knife which is particularly adapted for use in removing the semilunar cartilages from the knee.

The surgical removal of damaged semilunar cartilage from the human knee cavity, which desirably is done through a small incision anterior to the knee joint, presents several specific surgical difficulties. The incision is deepened through the skin and the subcutaneous tissue directly through the capsular structure of the knee. The anterior portion of the meniscus is quite easily detached from the tibia and the surrounding soft tissues, but as the cutting proceeds rearwardly to the posterior corner of the knee removal of this tissue becomes quite difficult. At this point the meniscus is held basically by two sets of strong collagenous fibers, namely, those running from the surface of the tibia onto the cartilagenous meniscus, and those running at a right angle to it, as extensions of the capsule of the knee joint.

One type of surgical knife currently used in the removal of semilunar cartilage from the knee consists of an elongated flat blade have a handle-engaging shank at one end, is curved slightly toward its forward end, and has a cutting edge at its front end. This type of knife is manufactured and sold by Rudolph Beaver, Inc., Belmont, Massachusetts. Another knife of the same general type is described in U.S. Pat. No. 3,221,744, consisting of an elongated body member the rear end of which serves as a handle. The body member has a curved cutting head near the front end thereof, and a removable and replaceable cutting blade is firmly supported upon the cutting head so that its cutting edge extends toward the front end of the instrument. When either of these two types of knife is used in knee surgery, the cutting edge is swept back in one of the aforementioned planes to cut the corresponding attachment, and then, after withdrawing the handle, the blade is turned through an angle of 90° so as to be positioned to cut those fibers constituting the other attachment. In either plane, the cutting edge is not visible to the surgeon, particularly from the posterior corner and beyond, and as a consequence the cutting edge is sometimes forced into and damages either the supporting structure at the posterior medial or the posterior lateral corners of the knee joint capsule, leading to latent instability. Should a surgical instrument of this type be pushed back against the knee joint, into the poplitial space where the major neural vascular structures of the lower extremity run through it, serious damage can result.

Another type of surgical instrument heretofore used for removing the cartilage from the knee has curved tracks which are inserted into the knee capsule for guiding a cutting blade slidable thereon. A form of this type of instrument is disclosed in U.S. Pat. No. 3,835,859 and includes a flexible track operatively connected to a handle and adapted to be extended therefrom into the knee cavity to conform to the interior configuration of the knee cavity, and a blade slidably mounted on the track and constrained to move thereon for cutting damaged or broken cartilage. Instruments of this type are cumbersome to use, and because of the restricted visibility at and beyond the posterior corner of the meniscus, a high degree of mechanical dexterity is required to ensure that insertion of the flexible wires constituting the track does not damage the supporting structure of the knee. Such instruments are also relatively expensive, adding to the already relatively high cost of performing this type of knee operation.

It is the object of the present invention to provide an improved surgical knife which is particularly adaptable for use in removing the semilunar cartilages from the knee which is simple in construction, relatively inexpensive to manufacture, amenable to sterilized packaging and which is disposable following use for a single procedure.

SUMMARY OF THE INVENTION

Briefly, the objects and purposes of the invention have been met by providing a surgical knife having an elongated handle-engaging shank and two cutting blades fixed to the forward end thereof. A first of the blades is flat transversely and concave longitudinally in extension of the shank with a curvature generally conforming to the curvature of the outer surface of the meniscus, and has a cutting edge at its front end. The second blade is integrally joined to the first blade along one edge thereof and is disposed at a right angle to the concave side of the first blade. At its forward end the width of the second blade is substantially equal to the width of the first blade and has a cutting edge disposed in a common plane with the cutting edge of the first blade. The second blade tapers rearwardly from its forward cutting edge toward the shank. A guide member projects forwardly from the point of intersection of the cutting edges of the two blades.

In use the under surface of the second blade is placed directly on the upper surface of the tibia and then forced into the knee cavity, simultaneously cutting with one sweep of the knife both sets of the collagenous fibers attached to the meniscus; the cutting edge of the second blade severs the fibers extending from the surface of the tibia, and the cutting edge of the first blade severs those fibers running at a right angle thereto. The top of the tibia serves as a guide for the second blade, and the outer surface of the meniscus serves as a guide for the curved portion of the first blade.

BRIEF DESCRIPTION OF THE DRAWINGS

Other objects, features and advantages of the invention will become apparent, and its construction better understood, from the following detailed description, taken in conjunction with the accompanying drawings, in which:

FIG. 1 is a greatly enlarged perspective view of the present invention showing a right-hand pattern thereof;

FIG. 2 is a top plan view of FIG. 1; and

FIG. 3 is a top plan view of the surgical knife of the invention showing a left-hand pattern thereof.

DESCRIPTION OF A PREFERRED EMBODIMENT

The illustrated preferred embodiment of the surgical knife 10 consists of an elongated, flat shank 12 formed of stainless steel and has a protruberance 14 at its rearward end to facilitate its being locked in a suitable handle 16. The shank in this embodiment is shaped and dimensioned to be received by and releasably locked in a suitable handle, such as the Beaver No. 2 handle sold by Rudolph Beaver, Inc. for use with the aforementioned Beaver surgical knife. The handle is preferably formed of stainless steel to permit its being steam autoclaved for re-use after disposal of the blade 10. A first blade 18 is an extension of the shank, and is flat transversely and concave longitudinally by virtue of curvature of the shank at 12a. The shank has a certain amount of flexibility and the curvature corresponds generally to the curvature of the outer surface of the meniscus of the human knee. The forward end of blade 18 is beveled at 18a to form a cutting edge, the bevel being on the convex side of the blade. The shank 12 and blade extension 18 typically has an overall length of about 6.5 centimeters, with about 2 centimeters of its length being forward from the point of curvature.

A second blade 20 is integrally joined along one edge of blade 18 and is disposed in a plane substantially at a right angle to the plane of blade 18, and on the concave side of blade 18. The forward end of blade 20, the width of which is equal to the width of blade 18, is beveled at 20a to form a cutting edge disposed in a plane common with the cutting edge 18a; the bevel 20a is on the upper side of blade 20. The width of blade 20 tapers gradually from front to back and merges with the shank 12 approximately at the point of curvature 12a; thus, the second blade 20 is typically about 2 centimeters long. In one embodiment, the width of shank 12 and blade 18, and the width of the forward edge of blade 20 is five millimeters; however, to facilitate removal of the meniscus when the knee ligaments are very tight, desirably the knife is also made in a smaller size, having a blade width of three millimeters.

It is evident from the foregoing description that the forward end of the knife has a pair of cutting edges 18a and 20a disposed perpendicular to each other. The guide member 22 projects forwardly from the point of intersection of the two cutting edges for facilitating insertion and manipulation of the knife.

The right-hand pattern of the surgical knife shown in FIGS. 1 and 2 is adapted for severing the meniscus disposed medially of an anterior incision. To facilitate cutting lateral to the anterior incision, the left-hand pattern of the knife shown in FIG. 3, which is a mirror image of the pattern shown in FIG. 2, would be used.

In use, the under surface of blade 20 is placed directly on the upper surface of the tibia and the knife swung in the plane of the meniscus to simultaneously cut both the ligaments from the tibia and from the knee capsule. The concave surface of blade 18 lays against the outer curved wall of the meniscus, the latter serving as a guide for its own removal. The projecting guide 22 guides the travel of the cutting edges helps prevent the fibers attached to the meniscus from falling away from the cutting edges of the knife. The shank 12 is sufficiently flexible to generally conform to the outer surface of the meniscus as the knife is inserted into the knee cavity. When both attachments to the meniscus are severed at the same time, the cartilage appears to swing out from the periphery of the knee capsule toward the center of the joint for easy removal in one smooth sweeping cut. Simultaneous cutting of both attachments greatly improves the visibility of the procedure, thereby to help minimize or eliminate inadvertent damage to the supporting structure at the posterior medial and/or posterior lateral corners of the knee. The knife can be fabricated by a stamping process, making it relatively inexpensive to manufacture, indeed, sufficiently low in cost that disposal of a blade after use in a single operative procedure is easily justified. The blade is preferably individually packaged in sterilized fashion so as to be conveniently available for insertion in a previously sterilized handle when needed. The knife is light in weight, not much different in weight or balance than the conventional Beaver-type of meniscus knife, and is easy to use. As has been suggested above, less dexterity is required to perform a meniscotomy with the present knife than with heretofore available surgical instruments.

Although a particular preferred embodiment of the invention has been described in detail above for illustrative purposes, it will be understood that variations or modifications of such disclosure, which come within the scope of the appended claims are fully contemplated. For example, the knife may be made in sizes other than those specifically mentioned. Also, although the blade has been described as adapted for removable attachment to a sterilizable handle, it is within the contemplation of the invention that the blade be permanently secured in a plastic handle, employing an injection molding process. In this case, both the blade and handle would be disposable. Further, although the shank and blades have been illustrated and described as being flat and of the same thickness throughout their widths, the shank and blades may be thicker along their edges to serve as guides.

I claim:

1. A surgical knife for the surgical removal of the meniscus from the human knee, comprising:
   an elongated, transversely flat, flexible shank of substantially uniform width throughout its length having a rearward end engageable with a handle and a forward end, said shank being curved near its forward end with a curvature generally corresponding to the curvature of the outer surface of the meniscus of the human knee and having first and second cutting blades fixed thereon at its forward end,
   said first blade being flat transversely and constituting a forward extension of the curved portion of said shank and having a transverse cutting edge across its extreme forward end disposed substantially perpendicular to the longitudinal axis thereof,
   said second blade being flat transversely and integrally joined to said first blade along one edge thereof and disposed on the concave said of said curved shank in a plane perpendicular to the plane of said first blade, and having a width at its forward end substantially equal to the width of said first blade and extending longitudinally rearwardly from the extreme forward end of said first blade and tapered at its rearward end to merge with said shank at a point forwardly of said curved portion, said second blade having a transverse cutting edge across the extreme forward end thereof disposed substantially perpendicular to the longitudinal axis thereof in a plane common with the cutting edge of said first blade and transversely of and perpendicular to the planes of said first and second blades.

2. A surgical knife according to claim 1, wherein said knife further comprises:
   a guide member integral with said blades projecting forwardly from substantially the point of intersection of the cutting edges of said first and second blades.

3. A surgical knife according to claim 1 or claim 2, wherein the width of said first and second blades at their forward end is in the range between about three millimeters and about five millimeters.

4. A surgical knife for the surgical removal of the meniscus from the human knee, comprising:

an elongated transversely flat, flexible shank having a rearward end engageable with a handle and a forward end being curved concavely near said forward end and first and second blades fixed thereon at its forward end, said first blade being flat transversely and constituting a forward extension from the curved portion of said shank and having a transverse cutting edge across the forward end thereof, said second blade being integrally joined to said first blade along one edge thereof and disposed on the concave side of said first blade in a plane perpendicular to the plane of said first blade, and having a width at its forward end substantially equal to the width of said first blade and extending rearwardly from the forward end of said first blade and tapered at its rearward end to merge with said shank at a point forwardly of said curved portion, said second blade having a transverse cutting edge at the forward end thereof, and a guide number integral with said blades projecting forwardly from substantially the point of intersection of the cutting edges of said first and second blades.

* * * * *